US012793834B2

(12) United States Patent
Stranjak et al.

(10) Patent No.: US 12,793,834 B2
(45) Date of Patent: Nov. 10, 2026

(54) DISTRIBUTED MEDICAL IMAGE PROCESSING

(71) Applicant: Siemens Healthineers AG, Forchheim (DE)

(72) Inventors: Armin Stranjak, Uttenreuth (DE); Swen Campagna, Engelthal (DE); Yan Tu Huang, Shenzhen (CN)

(73) Assignee: Siemens Healthineers AG, Forchheim (DE)

( * ) Notice: Subject to any disclaimer, the term of this patent is extended or adjusted under 35 U.S.C. 154(b) by 476 days.

(21) Appl. No.: 18/234,910

(22) Filed: Aug. 17, 2023

(65) Prior Publication Data

US 2024/0062879 A1 Feb. 22, 2024

(30) Foreign Application Priority Data

Aug. 18, 2022 (EP) .................................... 22190975

(51) Int. Cl.
*G16H 30/20* (2018.01)
*G06N 5/043* (2023.01)
(Continued)

(52) U.S. Cl.
CPC ............. *G16H 30/20* (2018.01); *G06N 5/043* (2013.01); *G06T 11/10* (2026.01); *G16H 40/20* (2018.01);
(Continued)

(58) Field of Classification Search
CPC ........ G16H 30/20; G16H 40/20; G16H 30/40; G16H 40/67; G06N 5/043; G06T 11/001;
(Continued)

(56) References Cited

U.S. PATENT DOCUMENTS 7,742,971 B2 * 6/2010 Sandholm .............. G06Q 30/08 705/37
2007/0244800 A1 * 10/2007 Lee ........................ G06Q 30/08 705/37
(Continued)

FOREIGN PATENT DOCUMENTS

EP 1041500 A2 * 10/2000 ............. G06Q 99/00
WO WO-9906932 A1 * 2/1999 ........... G06F 9/4875

OTHER PUBLICATIONS

Davis, Randall, and Reid G. Smith. "Negotiation as a Metaphor for Distributed Problem Solving." (1981). MIT AI Lab. A.I. Memo No. 624, May 1981. (Year: 1981).*
(Continued)

*Primary Examiner* — April Y Blair
(74) *Attorney, Agent, or Firm* — Banner & Witcoff, Ltd.

(57) ABSTRACT

A method of performing a medical imaging process, including: dividing a computing task of a medical imaging system unit into a set of sub-tasks, wherein the computing task is related to a generation of medical image data based on measurement data; selecting at least one sub-task of the set of sub-tasks for external execution; exchanging a sequence of signals including task delegation signals with a plurality of remote computing units, whereby the sequence of signals comprises at least one request signal sent by the medical imaging system unit; outsourcing the at least one selected sub-task to the selected remote computing unit for remotely generating a computing result of the at least one selected sub-task; receiving the generated computing result from the selected remote computing unit; and completing the computing task with the computing result received from the selected remote computing unit.

17 Claims, 8 Drawing Sheets

(51) Int. Cl.
*G06T 11/10* (2026.01)
*G16H 40/20* (2018.01)
*H04N 23/80* (2023.01)

(52) U.S. Cl.
CPC ......... *H04N 23/80* (2023.01); *G06T 2210/41* (2013.01); *G06T 2210/52* (2013.01)

(58) Field of Classification Search
CPC .. G06T 2210/41; G06T 2210/52; H04N 23/80
See application file for complete search history.

(56) References Cited

U.S. PATENT DOCUMENTS

| | | | | |
|---|---|---|---|---|
| 2015/0350109 | A1* | 12/2015 | Kiepfer | H04L 41/40 709/220 |
| 2017/0124730 | A1* | 5/2017 | Forman | G06T 11/006 |
| 2020/0027210 | A1* | 1/2020 | Haemel | G06T 7/10 |
| 2023/0410244 | A1 | 12/2023 | Campagna et al. | |

OTHER PUBLICATIONS

Middleton, Stuart E., Mike Surridge, Siegfried Benkner, and Gerhard Engelbrecht. "Quality of service negotiation for commercial medical grid services." Journal of Grid Computing 5, No. 4 (2007): 429-447. (Year: 2007).*
Cavrak, Igor, Armin Stranjak, and Mario Zagar. "Sdlmas: A Scenario Modeling Framework for Multi-Agent Systems." J. Univers. Comput. Sci. 15, No. 4 (2009): 898-925. (Year: 2009).*
Stranjak, Armin, Igor Čavrak, and Mario Žagar. "Scenario description language for multi-agent systems." In International Conference on Industrial, Engineering and Other Applications of Applied Intelligent Systems, pp. 855-864. Berlin, Heidelberg: Springer Berlin Heidelberg, 2008. (Year: 2008).*
Deen, S. Misbah. "A general framework for coherence in a CKBS." Journal of Intelligent Information Systems 2, No. 1 (1993): 83-107. (Year: 1993).*
Ramani, Sathish, and Jeffrey A. Fessler. "Parallel MR image reconstruction using augmented Lagrangian methods." IEEE transactions on medical imaging 30, No. 3 (2010): 694-706. (Year: 2010).*
Bennai, Mohamed T., et al. "Towards a generic multi-agent approach for medical image segmentation." In International Conference on Principles and Practice of Multi-Agent Systems, pp. 198-211. Cham: Springer International Publishing, 2017 (Year: 2017).*
Sandholm, Tuomas, and Victor R. Lesser. "Issues in automated negotiation and electronic commerce: Extending the contract net framework." In ICMAS, vol. 95, pp. 12-14. 1995. (Year: 1995).*
Vickrey, William. "Counterspeculation, auctions, and competitive sealed tenders." The Journal of finance 16, No. 1 (1961): 8-37. (Year: 1961).*
Cavrak I. Stranjak A. et al.: "SDLMAS: A Scenario Modelling Framework for Multi-Agent Systems" Journal of the JUCS 15(4): 898-925.
Stranjak, A. Cavrak I. et al.: (2011) "Scenario-Description Language in Multi-Agent Simulation System" in O'Shea, J. et al. (Eds.): KES-AMSTA LNAI (Spring-er-Verlag Berlin Heidelberg) 6682: 169-179.
Xue Hui et al: "Distributed MRI Reconstruction Using Gadgetron-Based Cloud Computing"; Magnetic Resonance in Medicine, John Wiley & Sons, Inc, United States, vol. 73, No. 3, pp. 1015-1025, XP002744683, ISSN: 1522-2594, DOI: 10.1002/MRM.25213; 2015.
Stranjak, A., Cavrak I., et al (2008) "Scenario Description Language for Multi-Agent Systems" In: Nguyen, N.T., Borzemski, L., Grzech, A., Ali, M. (Eds.) IEA/AIE LNCS (LNAI) (Springer, Heidelberg) vol. 5027: 855-864.
Middleton SE et al: "Quality of Service Negotiation for Commercial Medical Grid Services"; Journal of Grid Computing, Kluwer Academic Publishers, DO, vol. 5, No. 4, pp. 429-447, XP019551651, ISSN: 1572-9184, DOI: 10.1007/S10723-007-9080-X; 2007.
Stranjak Armin et al: "Decentralised Agent-Based Medical Image Reconstruction"; Procedia Computer Science, Elsevier, Amsterdam, NL, vol. 207, pp. 2106-2115, XP087203767, ISSN: 1877-0509, DOI: 10.1016/J. PROCS.2022.09.270 [retrieved on Oct. 19, 2022]; 2019.
Anonymous: "3.1 Client-server interaction—allocating a network address"; pp. 1-3, XP093012169, Retrieved from the Internet: URL:http://web.archive.org/web/20210511215 319/https://www.freesoft.org/CIE/RFC/2131/ 12.htm [retrieved on Jan. 9, 2023]; 2011.
Nicholas Petrick et al.: "Distributed Framework for Delivery of Medical Image Processing Algorithms", Proceedings of SPIE; vol. 4323; Aug. 1, 2001 (Aug. 1, 2001), pp. 222-228; XP093368711; DOI: 10.1117/12.435480; Retrieved from the Internet: URL:https://www.spiedigitallibrary.org/conference-proceedings-of-spie/ 4323/0000/Distributed-framework-for-delivery-of-medical-image-processing_algorithms/10.1117/12.435480.full?utm_source=chatgpt.com.

* cited by examiner

DISTRIBUTED MEDICAL IMAGE PROCESSING

TECHNICAL FIELD

The invention relates to a method of performing a medical imaging process. Further, the invention is directed to a method of performing a sub-task of a remote medical imaging system unit. Furthermore, the invention concerns a method of distributed performing of a medical imaging process of a medical imaging system. The invention also regards a medical imaging system unit. Besides, the invention pertains to a computing unit for performing a sub-task of a remote medical imaging system unit. The invention also applies to a medical imaging network.

BACKGROUND

Medical imaging processes (for example, MR imaging processes) depict the inside of the body of a patient, either in full or in part. Imaging techniques help doctors to diagnose a disease, assess its severity, and monitor sick patients. Most imaging procedures are painless, relatively safe and non-invasive. Medical imaging includes, for example, imaging techniques based on radiation, ultrasound scans and magnetic resonance imaging (abbreviated as MRI or MR imaging).

Imaging modalities, in particular, magnetic resonance imaging systems (abbreviated by MRI system or MR system), need substantial computing power for quickly performing preparation, execution, and evaluation, in particular, a reconstruction of images based on raw data of an imaging process. It is important that reconstructed images are available to the operator of a scan unit shortly after executing the measurement, i.e., the acquisition of raw data. A short time for image reconstruction is crucial, in particular, in emergency circumstances where a patient's health could be at risk.

For a magnetic resonance imaging system, two different approaches are conventionally used to achieve a sufficient speed of reconstruction. The first is to equip localized processing: This approach encompasses task processing on a localized computer system that is normally in close vicinity of devices that produce images, typically MR or CT scanners or any other medical imaging device. Such a solution is relatively effective but not scalable and highly expensive. With the development of modern imaging devices, it cannot fulfill ever-growing requirements for increased computational power, for example, due to a rise in imaging resolution or the number of receiving channels of an MR signal or an introduction of new compute-intensive applications like parallel image or compressed sensing.

The second approach includes an offloading of the computing task, especially the image reconstruction, somewhere else, for example, somewhere in the cloud, i.e., in a cloud computing system. This approach would solve the challenges of localized processing by providing an infrastructure to scale image processing by distributing processing tasks remotely. However, such cloud-based processing would be monolithic in nature; the tasks would not be compartmentalized or divided into smaller chunks. The tasks can naturally be big in size in terms of processing time and resources like the memory of CPU power, and therefore finding an appropriate computer system capable of executing such complex tasks could be a challenge. Furthermore, bandwidth can also be a problem in transporting huge task results at once between cloud nodes.

In order to tackle challenges concerning the second approach, a method that would divide tasks into smaller chunks in order to make the processing tasks more independent in terms of the requirements for high computing power, both locally and remotely, would be satisfactory. In this way, processing power requirements are not so stringent, and even smaller computing systems could participate in such processing activities since tasks are divided into smaller chunks in order to be manageable by the systems with less computing power.

However, another challenge emerges as a result of the complexity of task distribution in an open and competitive environment. If we imagine cloud-based computing resources distributed on the network with heterogeneous processing capabilities, it is obvious that such task distribution would require systematic and decentralized coordination between these resources and tasks in order to achieve efficiency and effectiveness of such task execution within a given time and processing costs.

Hence, there is a problem of an efficient organization of a distributed execution of a medical imaging task.

SUMMARY

The before-mentioned problem is solved by a method of performing a medical imaging process, a method of performing a sub-task of a remote medical imaging system unit, a method of distributed performing a medical imaging process of a medical imaging system, a medical imaging system unit, a computing unit for performing a sub-task of a remote medical imaging system unit, and a medical imaging network.

In the method of performing a medical imaging process, a computing task of a medical imaging system unit, also named a requestor, is divided into a set of possibly consecutive or partially parallel sub-tasks. The computing task is related to the generation of medical image data based on measurement data. At least one of the sub-tasks of the set of sub-tasks is selected for external execution, preferably by a remote computing unit that is not part of the "own" medical imaging system. In most cases, a remote computing unit, also named an executor, is spatially separated from the "own" medical imaging system. Hence, the remote computing unit provides a kind of external support to the medical imaging system unit. The medical imaging system unit comprises technical means for performing a computing task related to the medical imaging process of a medical imaging system. As later described in detail, such a computing task may comprise calculations for realizing a medical imaging process, in particular, a generation of protocol data, wherein the protocol data are intended to define a process for generating measurement data. Further, such a computing task may comprise a generation of reconstructed image data based on the measurement data. While the medical imaging system unit is part of a medical imaging system, the remote computing unit may be a part of a remote medical imaging system. However, the remote computing unit may also be a compute-only unit, i.e., a computer that is preferably separated from a medical imaging system and which offers its computing service to medical imaging systems, in particular, medical imaging system units.

Further, a sequence, i.e., a coupling sequence of signals comprising task delegation signals, is exchanged with a plurality of remote computing units, preferably via a distribution unit, for selecting at least one of the currently freely available remote computing units for execution of the selected sub-task. The sequence of task delegation signals comprises at least one request signal, preferably comprising a request for executing the selected sub-task sent by the medical imaging system unit for execution of the selected sub-task.

For finding a remote computing unit for executing the selected sub-task, a sequence of signals is exchanged. The sequence comprises task delegation signals exchanged with a plurality of remote computing units. The sequence of task delegation signals implements a dialogue between at least one medical imaging system unit and a plurality of remote computing units for arranging a coordinated performance of the task, in particular, for delegating the execution of the selected sub-task to one of the remote computing units. The sequence comprises the above-mentioned request for executing the selected sub-task and, preferably and further, as an answer to such a request, detailed information about performance and resources which the remote computing units are enabled to provide for the execution of the sub-task. The signals are exchanged preferably via a distribution unit with the remote computing units. The communication is performed for selecting at least one of the remote computing units for the execution of the selected at least one sub-task. Thereby, the sequence of task delegation signals comprises at least one request signal sent by the medical imaging system unit. The request signal comprises a request for executing the selected sub-task. As later described in detail, the communication for selecting an available appropriate remote computing unit for execution of the selected sub-task is preferably realized by an auction-like negotiation process. Such a negotiation process is preferably based on the second best estimation auction, also named "Vickrey auction", since by using such an auction type, the offers of the remote computing units are more realistic and encourage a truthful task execution estimation. Such an auction-like bidding process enables a selection of an optimal remote computing unit based on an amount of the resources for compensation of the remote execution of the sub-task available for the medical imaging system unit.

The distribution unit comprises a computer network (intranet or internet, preferably based on TCP/IP protocol. The distribution unit enables the inclusion of a plurality of medical imaging system units, also named requestors, and a plurality of remote computing units, also named executors, into the computer network. Such integration is simply a consequence of such internet protocol where every requestor holds a list of all available executors (via third-party application or directly) with which they communicate. As soon as a new executor appears or disappears from the network, the requestors, on demand, can refresh their lists. This can happen on demand (manually) or automatically via a third party.

The distribution unit implements a kind of "marketplace" which comprises an environment where interesting parties can offer their services and the other parties can ask for these services. It is normally a many-to-many relationship where a requestor can contact many executors, and an executor can be contacted by many requestors. Communication is normally one-to-one between any requestor and any executor, but as said, a requestor maintains several of these communication channels with many executors. It is called a "marketplace" as it is similar to "a market" where the exchange of services happens for a certain compensation (financial or exchange of available resources). Technologies or platforms like Web Services, a .NET distributed platform using a Communication Framework, Microservices or SDLMAS, etc., can be used for implementing such a distribution network.

After selecting the remote computing unit for performing the selected sub-task, the at least one selected sub-task is outsourced to the selected remote computing unit for remotely generating a computing result of the at least one selected sub-task.

Further, the generated computing result is received from the selected remote computing unit.

After that, the computing task is completed with the computing result received from the selected remote computing unit.

The computing task is related to the generation of image data based on measurement data and preferably to a control task for controlling an imaging process or a task for processing measurement data for generating image data. In particular, the computing task is related to the generation of control data to be transmitted to a scan unit and/or to the processing of raw data received from the scan unit. As later discussed in detail, the computing task related to the process of generating image data preferably includes a reconstruction task or a filtering task.

In particular, a complicated reconstruction task, for example, a parallel reconstruction, may be divided into sub-tasks.

Such a complicated reconstruction task may include one of the following reconstruction types:

Parallel reconstruction may be applied to an acquisition of different images in parallel (e.g., by interleaving k-space lines of different images) or by a computationally parallel image reconstruction of different images for whatever reason (e.g., because of a 3D-Fast Fourier Transformation or because raw-data flows in so rapidly), while the reconstruction of a single image is very computationally intensive and thus different images may be reconstructed in parallel then.

A complicated reconstruction task may also comprise an MRI "parallel imaging," which is an acquisition technique to generate an image by reducing the number of acquired k-space lines (by the use of multiple receive channels). Image reconstruction for this task is quite compute-intensive. Therefore, it is also advantageously divided into sub-tasks and distributed to different computing sources.

The set of consecutive sub-tasks may comprise a sequential order if the sub-tasks are all sequentially performed only by the local, i.e., the "own" medical imaging system unit. However, it is preferably intended to distribute at least one sub-task to a remote computing unit such that some sub-tasks are possibly processed in parallel.

Advantageously, computing resources can be accessed by remote medical imaging systems in a more flexible and optimized manner than in prior art. This is achieved by exchanging the above-mentioned task delegation signals with potentially available remote computing units. Using such a pre-defined and formalized protocol of task delegation signals enables a flexible combination of the computing capacity of any suitable and connectable computing units for performing a computing task in optimized conditions. Hence, high scalability of the execution of a medical imaging process is achieved since the number of requestors and executors is only limited by the throughput of the interconnecting infrastructure between the different units but not anymore by the individual processing power of the connected units. Individual remote computing units can vary in processing power or availability, but based on their offer during the delegation process, they can still compete for a service with a requestor if their offer is competitive enough. Further, high flexibility is achieved since selection rules and the amount of compensation can change on-the-fly in between delegation processes which brings complete flexibility to the choice of an executor. For example, the selection rules can change from processing time to image quality. For example, the requestor might decide to look after the fastest processing algorithm for its tasks immediately after it completes the negotiation and awards contracts to those executors based on the best image quality criteria. Furthermore, the method, according to the invention, comprises high robustness since executors and requestors can independently decide when to join or to leave the task delegation process.

In the method of performing a sub-task of a remote medical imaging system unit according to the invention, the above-mentioned sequence of signals is exchanged with the remote medical imaging system unit. In other words, the method of performing a sub-task of a remote medical imaging system unit comprises the common and complementary steps to the method of performing a medical imaging process for collectively performing a task using distributed computing units. The method can be performed preferably over a distribution unit. A distribution unit comprises the function of distributing sub-tasks from a medical imaging system unit to an available executor, i.e., an appropriate and available remote computing unit. In this context, it has to be mentioned that the presented method claim is written from the perspective of the remote computing unit, and the medical imaging system unit is a remote medical imaging system unit from the perspective of the remote computing unit. The sequence of signals comprises at least a request signal received from the remote medical imaging system unit. The request is related to an execution of a sub-task selected by the remote medical imaging system unit.

The sub-task is received by the remote computing unit, which is chosen for performing the sub-task from the remote medical imaging system unit, which is “remote” from the perspective of the remote computing units.

Then, the received sub-task is performed by the chosen remote computing unit, and a computing result of the sub-task is generated.

Then, the computing result is transmitted, preferably via the distribution unit, to the remote medical imaging system unit.

Advantageously, the capacity of any idle remote computing units, in particular, remote computing units of remote medical imaging systems, is enabled to be used for performing a complex task of a medical imaging system unit and for speeding up the process. This is achieved by exchanging a sequence of task delegation signals with a plurality of remote computing units, preferably via a distribution unit, for selecting at least one of the remote computing units for execution of the selected at least one sub-task. The exchange of the task delegation signals enables one to join a current available remote computing unit very flexibly based on deliberately predefined criteria. As later discussed in detail, such criteria may include some parameters of the computing process, for example, computing time or a level of image quality achieved by any remote computing unit. In this context, the task delegation process is used for finding out the optimum distribution of a task or the sub-tasks of the task onto at least one, preferably a plurality of remote computing units. Technical parameters, also named attributes, achievable by any remote computing units like image quality, required processing time, and also the “price to be paid,” i.e., the resources to be spent by the medical imaging system unit for performing these computing processes by the selected remote computing unit or the selected remote computing units, are enabled to be considered before a decision of committing a selected remote computing unit has been made. These attributes can also be combined together by weighting them, and simple addition or subtraction of these weighted attributes would give a simple value on which a medical imaging system unit can decide which remote computing unit to choose for performing a selected sub-task.

In the method of distributed performing of a medical imaging process of a medical imaging system according to the invention, a medical imaging system unit of the medical imaging system which is responsible for executing a computing task related to a medical imaging process acts according to the method of performing a medical imaging process. Further, in the above-mentioned method, at least one remote computing unit acts according to the method of performing a sub-task of a remote medical imaging system unit, according to the invention, in order to perform at least one sub-task of the medical imaging process. The method of distributed performing of a medical imaging process of a medical imaging system combines the advantages of the method of performing a medical imaging process and of the method of performing a sub-task of a remote medical imaging system unit according to the invention.

The medical imaging system unit, according to the invention, comprises a division unit for dividing a computing task into a set of sub-tasks. The computing task is related to the generation of medical image data based on measurement data. The division into sub-tasks is performed to distribute parts of the task to different computing resources such that the execution of the task can be accelerated.

The medical imaging system unit also includes a selection unit for selecting a sub-task of the sub-tasks for external execution. The selection unit, for example, selects a sub-task that needs particularly much computing time to solve. By outsourcing such a time-consuming sub-task, the overall computing time can be considerably reduced.

The medical imaging system unit further comprises a communication unit for exchanging a sequence of task delegation signals with a plurality of remote computing units, preferably via a distribution unit for selecting at least one of the remote computing units for execution of the selected sub-task. The sequence of task delegation signals comprises at least one request signal sent by the medical imaging system unit.

Part of the medical imaging system unit is also an outsourcing unit for outsourcing the selected sub-task to the selected remote computing unit for remotely generating a computing result of the selected sub-task. The medical imaging system unit further comprises a reception unit for receiving the generated partial computing result from the selected remote computing unit and also an execution unit for completing the computing task with the computing result received from the selected remote computing unit. The medical imaging system unit shares the advantages of the method of performing a medical imaging process.

The computing unit for performing a sub-task of a remote medical imaging system unit, according to the invention, comprises a communication unit for exchanging a sequence of signals with the remote medical imaging system unit, preferably over a distribution unit, whereby the sequence of signals comprises at least a request signal received from the remote medical imaging system unit.

The computing unit also comprises a reception unit for receiving the sub-task from the remote medical imaging system unit.

The computing unit further comprises an execution unit for executing the received sub-task and generating a computing result of the sub-task.

The computing unit also includes a transmission unit for transmitting the computing result, preferably via the distribution unit to the remote medical imaging system unit. The computing unit shares the advantages of the method for performing a sub-task of a remote medical imaging system unit.

The medical imaging network, according to the invention, comprises at least one medical imaging system unit according to the invention, at least one remote computing unit, according to the invention, and optionally a distribution unit for conveying communication between the at least one medical imaging system unit and the at least one remote computing unit. The medical imaging network shares the advantages of the method of distributed performing a medical imaging process of a medical imaging system.

A medical imaging network, according to the invention, may comprise at least one medical imaging system, comprising the medical imaging system unit according to the invention, preferably an MR imaging system. Such a medical imaging system comprises a scan unit for acquiring raw data from an object to be examined and, as the medical imaging system unit, preferably a local control device. If the medical imaging system comprises an MR imaging system, the local control device may include a measurement control unit and a reconstruction unit for reconstructing image data based on the acquired raw data. A task to be performed by the medical imaging system unit preferably comprises a reconstruction task of the reconstruction unit or a measurement control task of the measurement control unit. Advantageously, these complicated tasks can be completed based on a highly flexible pool of computing resources.

Preferably, the medical imaging system network includes an ensemble of at least two medical imaging systems, wherein each of the at least two medical imaging systems comprises a medical imaging system unit, according to the invention, and a remote computing unit for remotely generating a partial computing result of the selected sub-task. Advantageously, the different medical imaging systems are enabled to exchange selected sub-tasks dependent on current free calculating capacities such that a medical imaging process of all these medical imaging systems of the ensemble is accelerated as much as possible. In case of a network failure, the system returns to processing a complete task with one self-contained medical imaging system.

The remote computing unit preferably comprises a medical imaging system unit itself or, alternatively, a so-called compute-only source. A compute-only source is not necessarily assigned to a complete medical imaging system; quite the contrary, it may also include only a computer for calculating the results of sub-tasks. Advantageously, the at least one compute-only source enables to further speed up the medical imaging process. For example, the medical imaging system network preferably includes a dedicated computing cluster or one or more highly-performant computing machines with a single task of offering free computing resources that may be used by a medical imaging system which is still self-contained and can operate the complete task on its own in case of network issues. A big advantage of the medical imaging system network is that the additional computing power, i.e., the additional compute-only source, can easily be extended or renewed with a significantly higher frequency than the medical imaging system itself to benefit from the very short innovation cycles in the computing industry. Such a compute-only source can also be provided by a cloud computing system with, of course, higher latencies, but for some use cases, this may also be beneficial, for example, if a very high amount of computation work is required only in rare cases.

Some units or modules of the medical imaging network mentioned above can be completely or partially realized as software modules running on a processor of a respective computing system unit, e.g., on a local control device of a medical imaging system, in particular, a magnetic resonance imaging system or a CT-system, or on a remote computing unit.

A realization largely in the form of software modules can have the advantage that applications already installed on an existing computing system can be updated, with relatively little effort, to install and run these units of the present application. The object of the invention is also achieved by a computer program product with a computer program that is directly loadable into the memory of a computing system and which comprises program units to perform the steps of the inventive methods, at least those steps that could be executed by a computer when the program is executed by the computing system. In addition to the computer program, such a computer program product can also comprise further parts such as documentation and/or additional components, also hardware components such as a hardware key (dongle, etc.) to facilitate access to the software.

A computer-readable medium such as a memory stick, a hard disk, or other transportable or permanently-installed carrier can serve to transport and/or store the executable parts of the computer program product so that these can be read from a processor unit of a computing system. A processor unit can comprise one or more microprocessors or their equivalents.

In that context, it has to be mentioned that negotiation scenario description and runtime environment constitute contextual and conversation design limits for the negotiation and bidding process of multi-unit systems. The orientation to a language-independent description of a negotiation scenario as well as a ready-to-use platform for the provision of remote computing efficiency logic without the hurdle of implementing specific communication layers define a major criterion in the choice of such software platform. Preferably, SDLMAS language and platform can be chosen for realizing the software modules for the medical imaging network. Such a concept is described in Cavrak, Igor, Armin Stranjak, and Mario Zagar (2009) "SDLMAS: A Scenario Modelling Framework for Multi-Agent Systems" Journal of the JUCS 15(4): 898-925 and Stranjak, Armin, Igor Cavrak, and Mario Zagar (2008) "Scenario Description Language for Multi-Agent Systems" In Nguyen, N. T., Borzemski, L., Grzech, A., Ali, M. (Eds.) IENAIE LNCS (LNAI) (Springer, Heidelberg) vol. 5027: 855-864. SDLMAS explicitly provides expressive language for scenario description, independence between implementation details of an efficiency logic of different units, and provision of a platform, including code generation of necessary communication stack. It also proved to be a convenient platform for application in task scheduling. This is described in Stranjak, Armin, Igor Cavrak and Mario Zagar (2011) "Scenario-Description Language in Multi-Agent Simulation System" in O'Shea, J. et al. (Eds.): KES-AMSTA LNAI (Springer-Verlag Berlin Heidelberg) 6682: 169-179.

The dependent claims and the following description each contain particularly advantageous embodiments and developments of the invention. In particular, the claims of one claim category can also be further developed analogously to the dependent claims of another claim category. In addition, within the scope of the invention, the various features of different exemplary embodiments and claims can also be combined to form new, exemplary embodiments.

In a variant of the method of performing a medical imaging process according to the invention, the step of exchanging the sequence of signals includes the sub-step of sending a first request signal, also named a "call request signal," to the plurality of remote computing units, preferably via the distribution unit. The first request signal is intended to request as much remote computing units as possible to send their service proposals to the requesting medical imaging system unit. Further, the step of exchanging the sequence of signals comprises the sub-step of receiving a service proposal signal from at least one remote computing unit, preferably a group of one or preferably more remote computing units of the plurality of remote computing units, preferably via the distribution unit. Furthermore, the step of exchanging the sequence of signals comprises the sub-step of selecting at least one remote computing unit, preferably a group of the plurality of remote computing units, for executing the selected sub-task based on the received service proposal signal. A further sub-step comprises the step of sending a second request signal, preferably an outsourcing request signal for execution of the selected sub-task, to the selected remote computing unit and the step of receiving a commitment signal of the at least one remote computing unit for execution of the selected sub-task or a withdrawal of the proposal.

Preferably, the step of sending a second request signal comprises transmitting an offer to the selected, at least one currently freely available remote computing unit containing details of a criteria for a compensation of a remote execution of the selected sub-task with a quantitatively defined access to resources. Preferably, the offer contains the details about the functional definition of the award function, including already given values of the award function.

Preferably, the step of receiving a commitment signal comprises receiving a rejection or acceptance from the selected remote computing unit.

Preferably, the step of exchanging the coupling sequence of signals comprising task delegation signals includes at least one of the steps: a step of transmitting an answer signal to the selected remote computing unit. The answer signal includes an information of decline or commit for the compensation of a remote execution of the selected sub-task with a quantitatively defined access of the remote execution to resources, preferably technical resources. The quantitatively defined access to resources comprises a resource balancing that may comprise a "payment" based on an agreed award function. The "payment" may comprise the right to use the technical resources of the requesting medical imaging system unit; it also may include something like a real payment using monetary compensation. The right to use technical resources preferably comprises exclusive rights for computing time or a priority right to access to the computing power of the requesting medical imaging system unit.

The step of exchanging the coupling sequence of task selection signals preferably comprises the step of receiving an answer signal (or "re-answer signal") to the answer signal from the selected remote computing unit including an information message including the preferably partial computing result of the selected sub-task or no result. Advantageously, the requesting medical imaging system unit receives, in each case, information about the completion of the computing process of the remote computing unit. In case a partial result is received, the medical imaging system unit is enabled to complete its task based on the partial result. In case the medical imaging system unit receives information about the fact that no result is generated by the remote computing unit until a predetermined point in time, the medical imaging system unit is enabled to react to such dysfunction by re-distributing the sub-task or by completing the selected sub-task by itself.

The step of exchanging the coupling sequence of signals also preferably comprises the step of transmitting a compensation signal. The compensation signal comprises information about a compensation of the remote execution of the selected sub-task by a quantitatively defined access to resources to the selected remote computing unit. Such compensation preferably comprises an award for the execution of the selected sub-task. The amount of the compensation, preferably an award, is preferably based on the reception time of the result and the offer. Hence, the compensation is scalable and adaptable to the performance of the selected remote computing unit such that there is a stimulus for the remote computing unit to perform the selected sub-task with the highest possible performance.

In a variant of the method of performing a medical imaging process according to the invention, the request signal, which may be the first and/or the second request signal, comprises details about the sub-task to be executed. These details preferably comprise an algorithm name and version which are known to the currently freely available remote computing unit in advance and/or criteria for a compensation of a remote execution of the selected sub-task with a quantitatively defined access to resources, in particular, the award promised to the winning bidder.

Preferably, the service proposal signal comprises an estimated time by which the sub-task can be executed by the remote computing unit. Advantageously, the medical imaging system unit is enabled to select a remote computing unit for performing the selected sub-task based on an estimated time for the execution of the sub-task. In particular, the medical imaging system unit is enabled to select a remote computing unit, the estimated time of which matches to the time planned by the medical imaging system unit for the sub-task.

In a variant of the method of performing a medical imaging process according to the invention, the compensation signal transmitted to the selected remote computing unit comprises an award for compensation for the execution of the selected sub-task. Advantageously, the award is used as a means of compensation for the remote execution of the selected sub-task.

Preferably, the request signal, which may be the first and/or the second request signal, comprises a preferably guaranteed award value if the sub-task is executed at the estimated time estimated by the selected remote computing unit and a maximum award value if the sub-task is executed earlier. Advantageously, there is a motivation for the selected remote computing unit to perform the selected sub-task as fast as possible.

In a variant of the method of performing a medical imaging process according to the invention, the step of sending a second request signal comprises transmitting an offer from the requesting medical imaging system unit to the selected remote computing unit, and the offer includes a criteria for a compensation of a remote execution of the selected sub-task with a quantitatively defined access to resources and the criteria includes details about the shape of the functional definition of an award function. The award function preferably includes an already given guaranteed award value, a maximum award value, as well as a time of the deadline, representing the deadline after which an award value will not be offered. Advantageously, the selected remote computing unit is informed about the details of the offered compensation, such that it is enabled to make a realistic offer of performing the selected sub-task. The deadline enables the calculation of a time limit until the selected sub-task is completed by the selected remote computing unit. Otherwise, the remote control unit does not get any compensation for executing the sub-task.

Preferably, the task to be performed comprises a reconstruction task for parallel image reconstruction based on sub-sets of parallel acquired raw data, and each of the sub-tasks comprises a reconstruction of a partial image based on a different sub-set. Advantageously, these sub-tasks are enabled to compute in parallel using the methods according to the invention.

Preferably, the computing task includes at least one of the following types of control tasks: controlling a scan unit of the medical imaging system or reconstructing image data based on raw data acquired by a scan unit of the medical imaging system. Advantageously, the time requirement for completing these tasks can be reduced by performing sub-tasks in parallel by selected remote computing units.

Preferably, the execution unit of the medical imaging system unit is arranged to locally execute a sub-task if outsourcing this sub-task is not appropriate according to a predefined criterion. A predefined criterion may comprise that the local execution is more efficient, preferably with respect to aspects of time consumption or the existence of free local computing resources.

In other words, the outsourced sub-task is locally executed by the execution unit of the local medical imaging system unit by default. "By default" means that the outsourced sub-task is executed by the local execution unit based on the above-mentioned criterion. The above-mentioned criterion preferably includes the decision of local execution of the sub-task in case no result is received from the remote computing unit processing the outsourced sub-task. Advantageously, the local control unit is self-contained.

In a variant of the medical imaging system unit according to the invention, the execution unit is arranged to detect, as a special type of predefined criterion, the status of one or more completed consecutive sub-tasks to determine based on the detected status if the computing result generated by the remote computing unit is received by the medical imaging system unit or will be received on time. Hence, it is detected if it is necessary to start the related sub-task by the medical imaging system unit by default. Further, the medical imaging system unit is arranged to execute the computing task based on the received computing result if the partial computing result is received on time or alternatively to execute the selected sub-task itself if the partial computing result is not received on time. Advantageously, the computing task can be completed in any case without any delay compared to a completely local execution of the computing task.

In a variant of the medical imaging system unit according to the invention, a task to be computed includes at least one of the following types of tasks:

a. controlling a scan unit of the related medical imaging system,
b. reconstructing image data based on raw data acquired by a scan unit of the medical imaging system.

Advantageously, the generation of control data or a sub-task of a reconstruction task can be relocated to different computing resources for accelerating a control process or reconstruction process.

In another variant of the medical imaging system unit according to the invention, the sequence of tasks to be processed is implemented as a queue of consecutive sub-tasks. The queue determines an unambiguous order of processing the consecutive sub-tasks, particularly in case the sub-tasks are performed by the medical imaging system unit. Advantageously, an order for processing the different sub-tasks is generated. For example, the order can be determined based on available input data or based on the consumption of time the different sub-tasks need.

In a further variant of the medical imaging system unit according to the invention, the remote computing unit includes a remote medical imaging system unit of a different medical imaging system. Advantageously, computing resources of medical imaging systems, which are usually only used when an imaging process is running, can be exploited over the whole time if they are accessed by remote medical imaging systems.

Preferably, in a variant of the medical imaging system unit, according to the invention, the remote computing unit includes a cluster comprising a plurality of medical imaging system units of different medical imaging systems. Advantageously, every medical imaging system that has idle computing power can be used to execute sub-tasks. Thus, they form a kind of virtual cluster, distributed and dynamically available. Further, the local medical imaging system unit, according to the invention, itself may be arranged to offer its computing power to other remote medical imaging systems if it is idle itself.

In a preferred variant of the medical imaging system unit, according to the invention, the remote computing unit is located in a cloud computing system. Advantageously, the remote computing source can also be provided as a virtual resource in a cloud computing system without an actual existence of an additional remote medical imaging system.

Preferably, the medical imaging system, according to the invention, comprises at least one of the following:

a. a magnetic resonance imaging system,
b. an X-ray imaging system, preferably a CT-imaging system,
c. an ultrasound imaging system.

A magnetic resonance imaging method comprises, additionally to the acquisition of raw data, a plurality of processing steps. These processing steps preferably include processing steps for preparing the raw data for the reconstruction of image data, the reconstruction of image data itself, and further steps for generating image data, for example, the application of additional reconstruction algorithms, the combination of partial images to a combined image and post-processing steps for corrections of movements. Further, the steps for generating image data preferably comprise at least one of the steps for generating an evaluation of time series, steps for detection of anatomical structures, steps for performing a functional magnetic resonance imaging, steps for performing diffusion imaging, steps for performing a perfusion imaging and steps for performing filtering methods.

Preferably, the reconstruction is divided into a plurality of sub-tasks, which are transmitted to remote computing resources. Further, also the following steps like application of additional reconstruction algorithms, post-processing steps for corrections of movements, evaluation of time series, detection of anatomical structures, functional magnetic resonance imaging, diffusion imaging, perfusion imaging, and filtering methods, are preferably divided into sub-tasks and outsourced to remote computing units.

Input data for a sub-task are typically either pre-processed raw data or reconstructed images (the latter especially for post-processing), but this is strongly dependent on the concrete algorithm or even variant. Intermediate points could make sense, but in practice, these two are the most relevant ones. For example, both filtering and motion correction can be done either in the early stages of the image recon pipeline or on the reconstructed images, depending on the concrete algorithm. In practice, we have to identify a concrete point in the reconstruction pipeline at which it makes sense for the individual concrete use case from which the external computation would make sense. For example, in the case of alternative reconstructions on the basis of the same raw data, this would be at a very early stage of the pipeline (directly after system-dependent pre-processing/normalization of the raw data), even if the original reconstruction offloaded only, e.g., post-processing tasks (e.g., because the medical images, in particular, MR images, are acquired sequentially over time).

A CT-imaging method comprises the steps of receiving raw data from a scan unit, a preparation step for generating corrected and re-arranged raw data. The actual CT reconstruction step for generating image data is based on the prepared raw data and a filtering step. In CT-imaging, a plurality of different sets of image data can be generated based on the same set of raw data using different sets of parameters for reconstruction. All these reconstructions can be implemented as sub-tasks performed on different remote computing units. Further, a filtering step is carried out on the generated image data. Also, the filtering step can be carried out by the different remote computing units or, alternatively by a local medical imaging system unit.

BRIEF DESCRIPTION OF THE DRAWINGS

The invention is explained below with reference to the figures enclosed once again. The same components are provided with identical reference numbers in the various figures.

The figures are usually not to scale.

DETAILED DESCRIPTION

Figure 1:
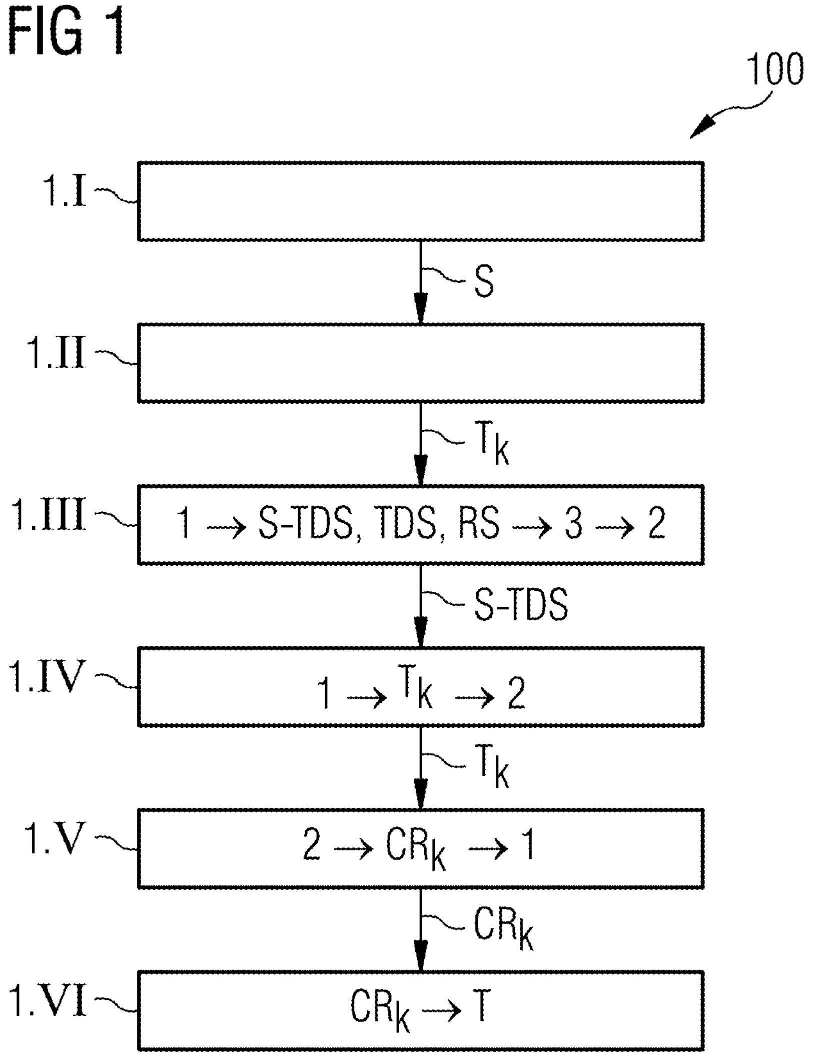
FIG. 1 shows a flow chart illustrating a method of performing a medical imaging process of an MR imaging system according to an embodiment of the invention.

FIG. 1 shows a flow chart 100 illustrating a method of performing a medical imaging process of an MR imaging system according to an embodiment of the invention.

In step 1.I, a computing task T is received by a medical imaging system unit 1, for example, from a control unit of a medical imaging system, and the received task T is divided into a set S of sub-tasks $T_1, \ldots, T_n$. The task T to be processed is related to the generation of medical image data based on measurement data.

In step 1.II, one sub-task $T_k$ of the sub-tasks $T_1, \ldots, T_n$ of the set S of sub-tasks $T_1, \ldots, T_n$ is selected for external execution (n is a natural number, 1<=k<=n).

In step 1.III, a sequence S-TDS of task delegation signals TDS is exchanged with a plurality of remote computing units 2 via a distribution unit 3 for selecting at least one of the remote computing units 2 for the execution of the selected sub-task $T_k$. The sequence S-TDS of task delegation signals TDS comprises at least one request signal RS sent by the medical imaging system unit 1.

In step 1.IV, the selected sub-task $T_k$ is outsourced to the selected remote computing unit 2 for remotely generating a computing result $CR_k$ of the selected sub-task $T_k$.

In step 1.V, the generated computing result $CR_k$ is received by the medical imaging system unit 1 from the selected remote computing unit 2.

In step 1.VI, the computing task T is completed based on the computing result $CR_k$ received from the selected remote computing unit 2.

Figure 2:
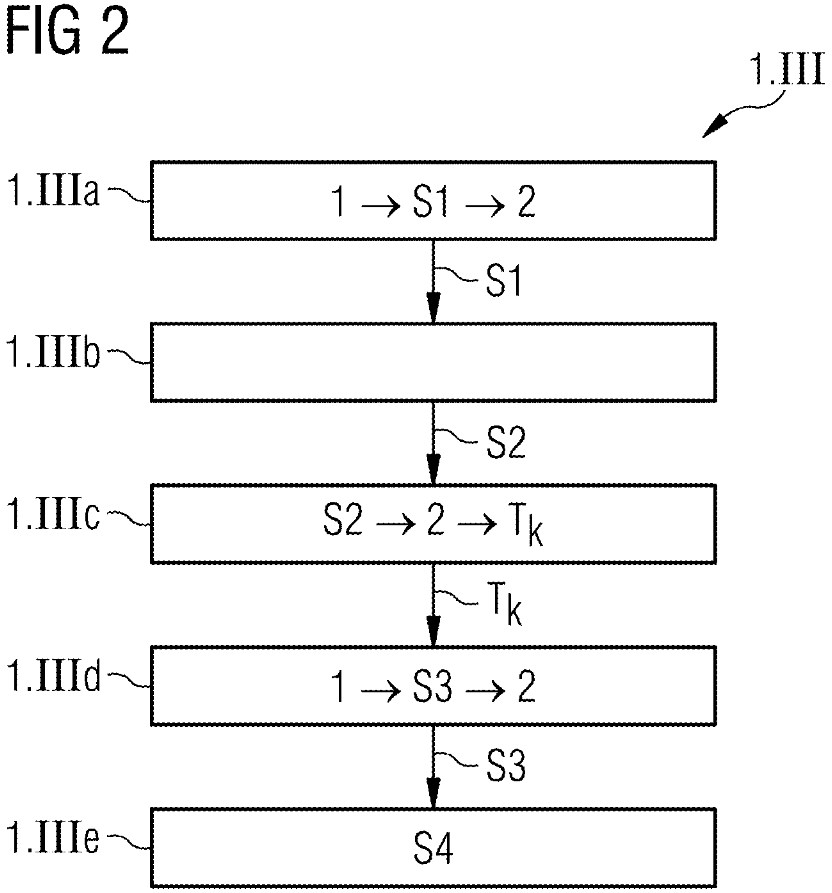
FIG. 2 shows a flow chart illustrating step 1.III of the method of performing a medical imaging process of an MR imaging system shown in FIG. 1.

In FIG. 2, a flow chart concerning step 1.III of the method of performing a medical imaging process of an MR imaging system shown in FIG. 1 is illustrated.

In step 1.III, exchanging of a sequence S-TDS of signals includes the following sub-steps:

In sub-step 1.IIIa, a first request signal S1, i.e., a "call request signal," is sent as a kind of broadcast signal via the distribution unit 3 to the plurality of remote computing units 2. The "call request signal" requests all available remote computing units 2 for sending a service proposal signal S2 to the requesting medical imaging system unit 1.

In sub-step 1.IIIb, a service proposal signal S2 is received from a group of the remote computing units 2, which have received the first request signal S1 and are, in principle, available for performing a sub-task $T_k$ of the requesting medical imaging system unit 1.

In sub-step 1.IIIc, at least one remote computing unit 2 of the group of remote computing units 2 is selected by the medical imaging system unit 1 for executing the selected sub-task $T_k$ based on the received service proposal signal S2.

In sub-step 1.IIId, a second request signal S3, i.e., an outsourcing request signal, is sent for the execution of the selected sub-task $T_k$ to the selected remote computing unit 2.

In sub-step 1.IIIe, a commitment or proposal withdrawal signal S4 of the selected remote computing unit 2 for the execution of the selected sub-task $T_k$ is sent from the selected remote computing unit 2 to the medical imaging system unit 1.

Figure 3:
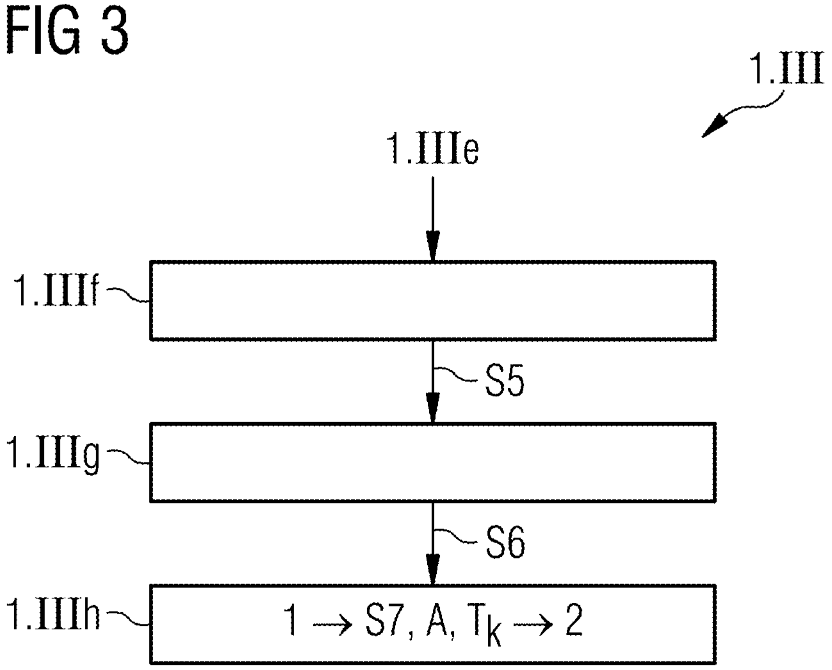
FIG. 3 shows a flow chart illustrating sub-steps 1.IIIf to 1.IIIh of step 1.III of the method of performing a medical imaging process of an MR imaging system shown in FIG. 1.

FIG. 3 shows a flow chart illustrating optional sub-steps 1.IIIf to 1.IIIh of step 1.III of the method of performing a medical imaging process of an MR imaging system shown in FIG. 1.

In sub-step 1.IIIf, an answer signal S5 is transmitted to the selected remote computing unit 2, including information of decline or commit for the compensation of remote execution of the selected sub-task $T_k$ with a quantitatively defined access to resources. Such a quantitatively defined access to resources can be realized as a payment based on an agreed award function. In that context, it has to be mentioned that a "payment" is not restricted to a commercial transaction; it may also include a formal clearing of supplied performances.

In sub-step 1.IIIg, an answer signal S6 to the answer signal S5 to the selected remote computing unit 2 is received by the medical imaging system unit 1 from the selected remote computing unit 2. The answer includes an information message including the partial computing result $CR_k$ of the selected sub-task $T_k$ or no result for the case that the remote computing unit 2 was not able to perform the sub-task $T_k$ and to provide the expected partial computing result $CR_k$.

In sub-step 1.IIIh, a compensation signal S7, comprising an award A as compensation for the remote execution of the selected sub-task $T_k$ is transmitted from the medical imaging system unit 1 to the selected remote computing unit 2. Award A is a type of a quantitatively defined access to resources. Award A can be determined based on the actual reception time $T_r$ of the result $CR_k$ and the offer.

Figure 4:
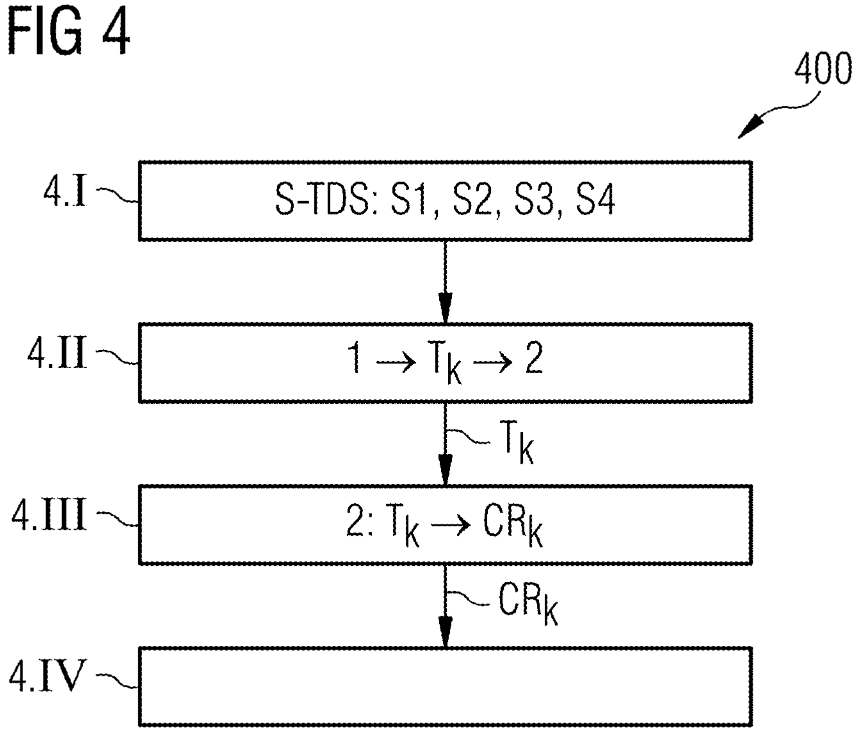
FIG. 4 shows a flow chart illustrating a method for executing a sub-task of a medical imaging system unit according to an embodiment of the invention.

FIG. 4 shows a flow chart 400 illustrating a method for performing a sub-task $T_k$ of a remote medical imaging system unit 1 according to an embodiment of the invention. The method is described from the perspective of performing remote computing unit 2.

In step 4.I, a sequence S-TDS of task delegation signals TDS is exchanged by the remote computing unit 2 with the remote medical imaging system unit 1 over a distribution unit 3, whereby the sequence S-TDS of signals TDS comprises a request signal S1 for the execution of the sub-task $T_k$ received from the remote medical imaging system unit 1.

In step 4.II, the sub-task $T_k$ is received from the remote medical imaging system unit 1.

In step 4.III, the received sub-task $T_k$ is executed, and a computing result $CR_k$ of the sub-task $T_k$ is generated by the remote computing unit 2.

In step 4.IV, the computing result $CR_k$ is transmitted via the distribution unit 3 to the remote medical imaging system unit 1.

Figure 5:
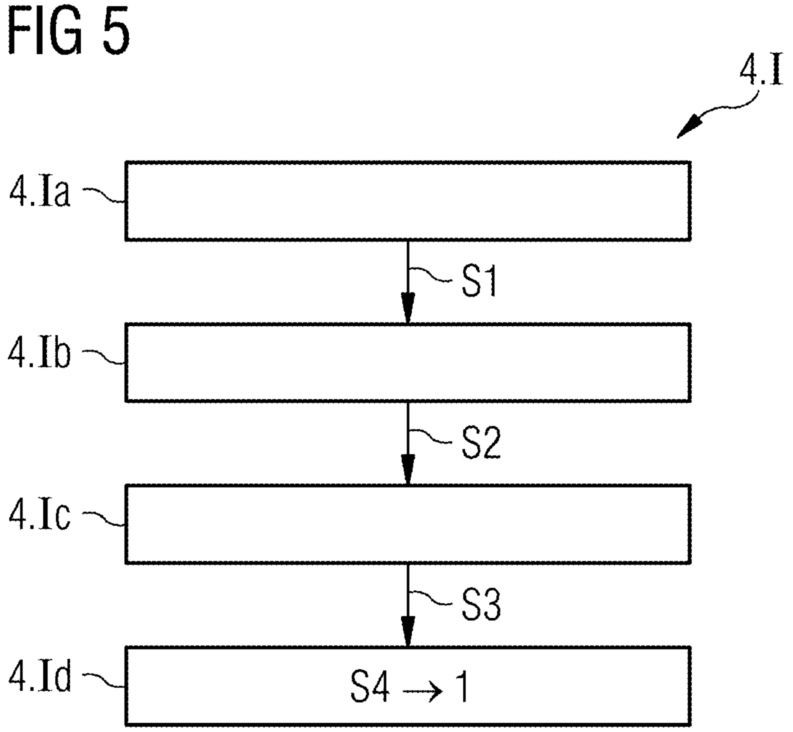
FIG. 5 shows a flow chart illustrating step 4.I of the method of performing a sub-task of a medical imaging system unit shown in FIG. 4.

In FIG. 5, a flow chart illustrating step 4.I of the method for executing a sub-task $T_k$ of a medical imaging system unit 1 shown in FIG. 4 is depicted. Step 4.I comprises the step of exchanging a sequence S-TDS of task delegation signals TDS.

In sub-step 4.Ia, a first request signal S1, i.e., a call request signal, is received by the remote computing unit 2 from the medical imaging system unit 1 via the distribution unit 3.

In sub-step 4.Ib, a service proposal signal S2 is sent from the remote computing unit via the distribution unit 3 to the medical imaging system unit 1.

In sub-step 4.Ic, a second request signal S3, i.e., an outsourcing request signal for execution of the selected sub-task $T_k$ is received by the selected remote control unit 2 from the medical imaging system unit 1.

In sub-step 4.Id, a commitment or proposal withdrawal signal S4 for the execution of the selected sub-task $T_k$ is sent from the selected remote control unit 2 to the medical imaging system unit 1.

Figure 6:
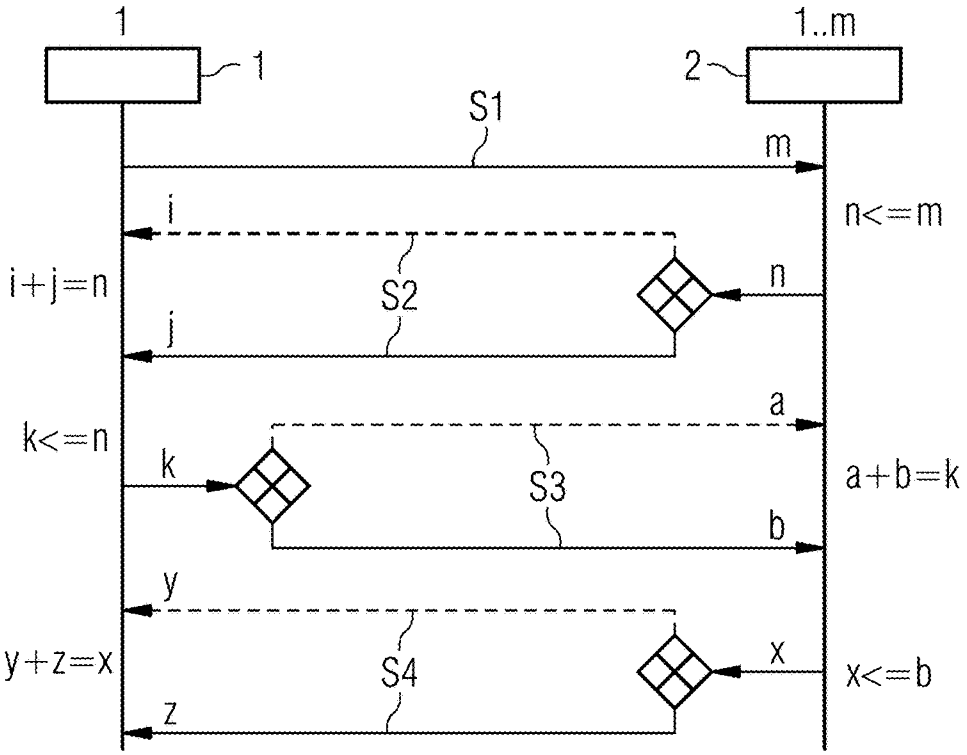
FIG. 6 shows a schematic diagram illustrating the communication in a medical imaging network according to an embodiment of the invention.

In FIG. 6, a schematic diagram illustrating the communication in a medical imaging network 10 (shown in FIG. 7) according to an embodiment of the invention is shown.

On the upper left side of the schematic diagram, a medical imaging system unit 1, also named as the requestor, is depicted, and on the right side of the schematic diagram, a remote computing unit 2, also named as executor, is depicted. The medical imaging system unit 1 on the left side symbolizes one single medical imaging system unit 1 (symbolized by the number "1" above the schematic rectangle related to the medical imaging system unit 1. However, the remote computing unit 2 on the right side symbolizes a plurality of m remote computing units 2 (m is a natural number), which is illustrated by "1 . . . m" above the schematic rectangle symbolizing the remote computing units 2.

In a first step, a service request signal, i.e., a "call for service" S1, is sent to all m registered remote computing units 2 of the medical imaging network 10. In a second step, the medical imaging system unit 1 waits for an answer from the remote computing unit 2 with a predetermined deadline.

Further, the medical imaging system unit 1 receives some service proposal, or refusal signals S2 from n remote computing units 2, wherein n is a natural number and n<=m. Indeed, only j remote computing units 2 send a service proposal to the medical imaging system unit 1 and i remote computing units 2 send a service refusal back to the requesting medical imaging system unit 1, wherein i, j are natural numbers and i+j=n. The square standing on a corner symbolizes the possible different types of answers, i.e., the service proposal or refusal.

The medical imaging system unit 1 considers the proposals from the j remote computing units 2 based on an internal logic. The internal logic can be based on a resource allocation system, wherein provided resources are quantitatively cleared. For example, such a resource includes an amount of provided processing time, and the remote computing unit 2 with the shortest processing time is favored.

In a third step, based on an internal selection, the medical imaging system unit 1 transmits a signal S3 to k remote computing units 2 (k is a natural number and k<=n), including information about an acceptance or rejection of their bids. For example, to a number of "a" remote computing units 2 (a is a natural number), a rejection is sent, and to a number of b remote computing units 2 (b is a natural number), a proposal of acceptance is sent, wherein a+b<=k.

In a fourth step, a commitment or proposal withdrawal signal S4 is sent from the remote computing units 2 to the medical imaging system unit 1. In detail, x remote computing units 2 (x is a natural number and x<=b) send a final answer to the medical imaging system unit 1. A number of z remote computing units 2 (z is a natural number and z<=x) send a final commitment message to the medical imaging system unit 1, and this message will bind both sides into a contracting obligation. Further, y remote computing units 2 send a proposal withdrawal to the medical imaging system unit 1 (y is a natural number, and y+z=x).

Figure 7:
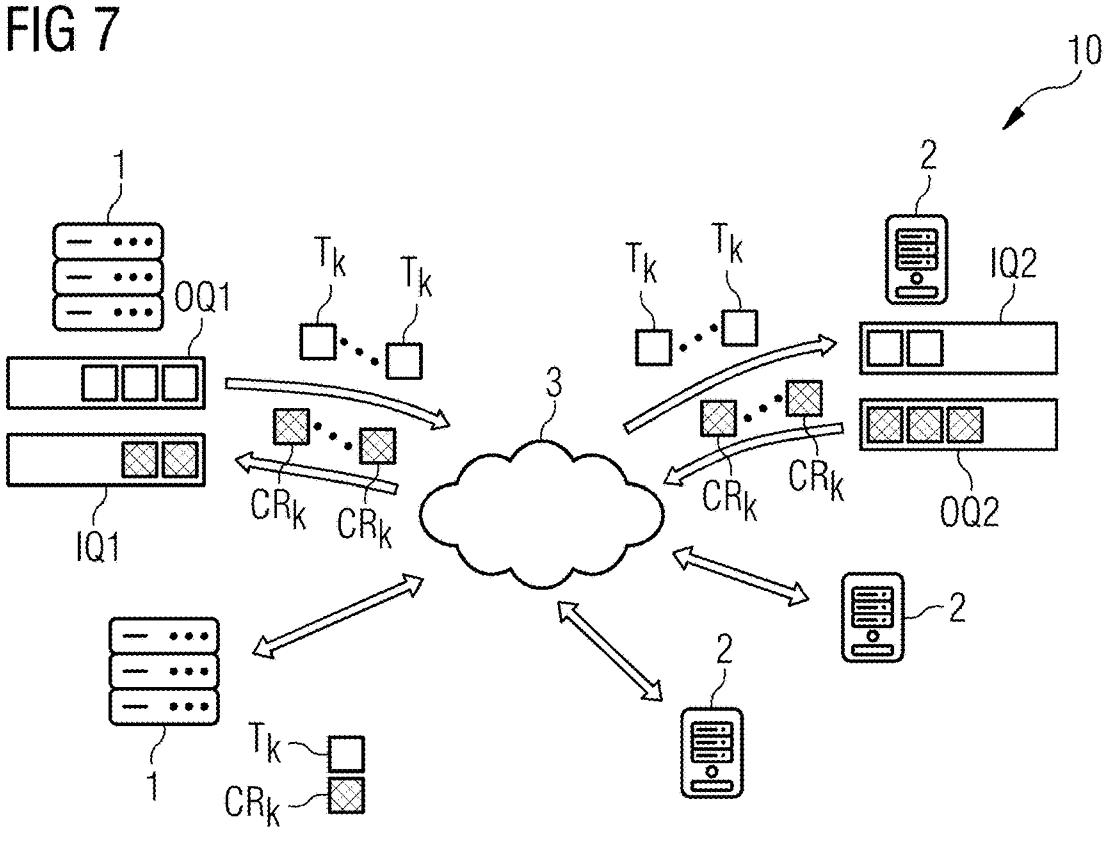
FIG. 7 shows a schematic representation illustrating a medical imaging network according to an embodiment of the invention.

In FIG. 7, a schematic representation illustrating a medical imaging network 10 according to an embodiment of the invention is depicted.

The medical imaging network 10 comprises a plurality of medical imaging system units 1, a plurality of remote computing units 2, and a distribution unit 3. The distribution unit 3 provides a type of technical distribution node for connecting and assigning requesting medical imaging system units 1 and potentially executing remote computing units 2. Each of the medical imaging system units 1 includes an output queue OQ1, including sub-tasks $T_k$ to be outsourced to the remote computing units 2 and an input queue IQ1 for receiving results $CR_k$ of executed sub-tasks $T_k$. Correspondingly, each remote computing unit 2 also comprises an input queue IQ2 for receiving sub-tasks $T_k$ to be executed and an output queue OQ2 for outputting results $CR_k$ to the remote medical imaging system units 1 from which the corresponding sub-tasks $T_k$ have been received. The distribution unit 3 receives and distributes these transmitted sub-tasks $T_k$ and results $CR_k$ to the addressed units 1, 2.

Figure 8:
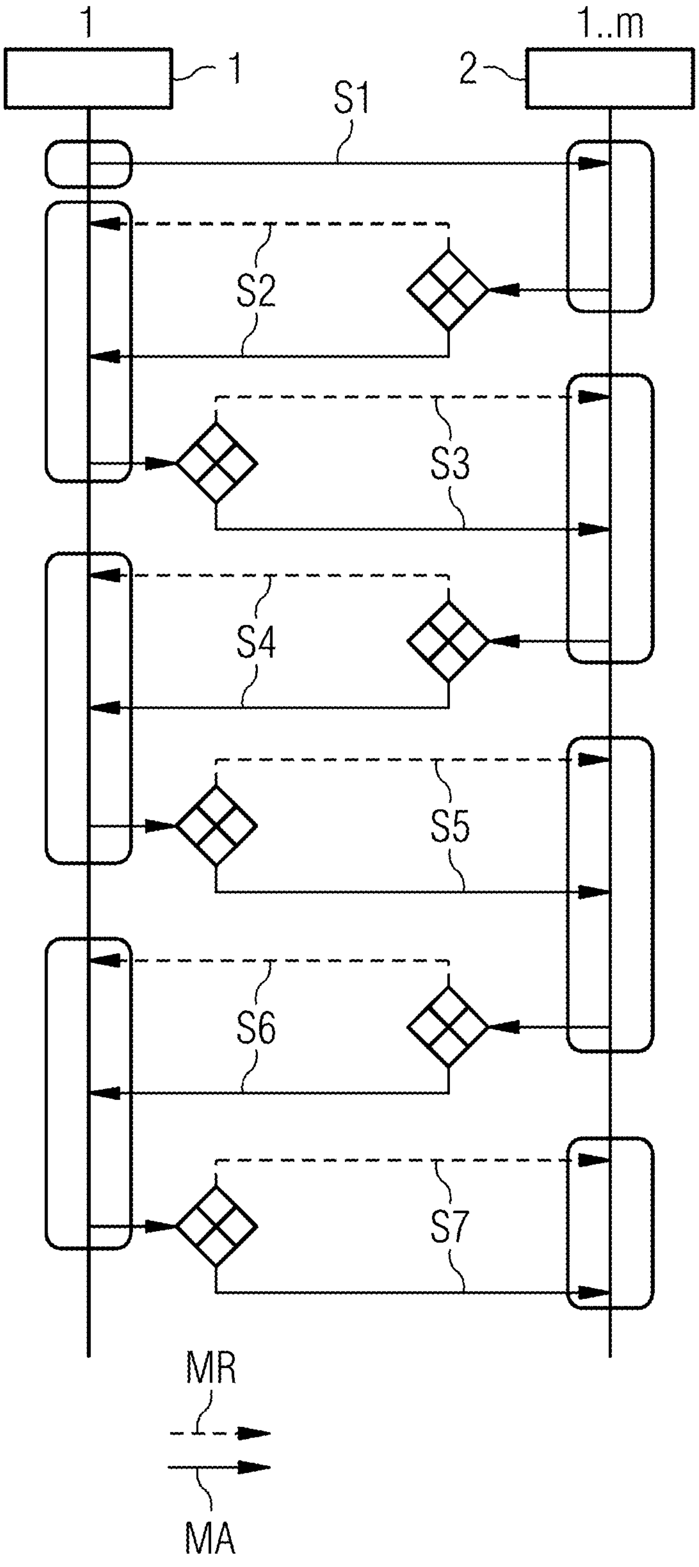
FIG. 8 shows a schematic diagram illustrating the communication in a medical imaging network according to a second embodiment of the invention.

In FIG. 8, a schematic diagram illustrating the communication in a medical imaging network according to a second embodiment of the invention is depicted. Messages of rejection MR are symbolized by an arrow with a dashed line, and messages of acceptance MA include an arrow with a solid line.

Similar to the embodiment shown in FIG. 6, on the upper left side of the schematic diagram, a medical imaging system unit 1, also named as the requestor, is depicted, and on the right side of the schematic diagram, a remote computing unit 2, used as executor, is depicted. The medical imaging system unit 1 on the left side symbolizes one single medical imaging system unit 1 (symbolized by the number "1" above the schematic rectangle related to the medical imaging system unit 1). However, the number of one medical imaging system unit 1 is only chosen for the sake of simplicity, and it is explicitly mentioned that the invention is also directed to a plurality of medical imaging system units 1. Similar to FIG. 6, the remote computing unit 2 symbolizes a plurality of m remote computing units 2 (m is a natural number).

In a first step, as soon as a requestor identifies a need for additional resources to complete its task, T, the requestor 1 starts a negotiation conversation with all identified and available executors 2.

This is formally initiated with the transmission of a message named a "call for proposal" (by short CFP) S1, which is sent to all m registered remote computing units 2. The content of this "call for proposal" message contains the details about the task that needs to be executed. These details typically include an algorithm name and a version number, which are known to the executors 2 in advance, and the award A promised to the winning bidder 2. The data values needed for task execution, normally do not have any significant influence on the execution time and therefore the data are provided later only to the winning executor 2.

In a second step, the medical imaging system unit 1 waits for an answer from the remote computing units 2 with a predetermined deadline. All these potential executors 2 consider a task execution request and provide their bids.

Based on an award function, the requestor 1 provides only a guaranteed award value $A_0$ if the sub-task $T_k$ is executed at the time estimated by the winning executor 2 as well as a maximum award value $A_m$ if the task is executed earlier. Based on these two values $A_0$, $A_m$, executors 2 consider such offers and by sending a message with a performative PROPOSE (solid line), they provide the estimated time $T_e$ which runs out, when the sub-task $T_k$ is completed. Alternatively, the executors 1 simply reject the "call for proposal" by sending terminating performative NO-PROPOSAL (dashed line). Upon reception of all bids or the expiration of a given timeout period, the requestor 1 chooses the winning bid from the received vector of estimated times $T_e$ by selecting the executor 2 with the shortest estimated time $T_e$ for the sub-task execution. In order to ensure that executors 2 will use their dominant bidding strategy by truthfully revealing their time execution evaluation, the negotiation is based on second best estimation auction (Vickrey auction). Therefore, the requestor 1 chooses the winning executor 2, but it offers estimated time $T_e$ from the second best offer. In such way, it is in the executor's interest to bid truthfully their estimation.

Hence, in the second step, the medical imaging system unit 1 receives some service proposal or refusal signals S2 from n remote computing units 2, wherein n is a natural number and n<=m.

The medical imaging system unit 1 considers proposals from the remote computing units 2 based on an internal logic. The internal logic can be based on a resource allocation system, wherein provided resources are quantitatively cleared. For example, the resources include an amount of provided processing time and the shortest processing time is favoured.

Figure 10:
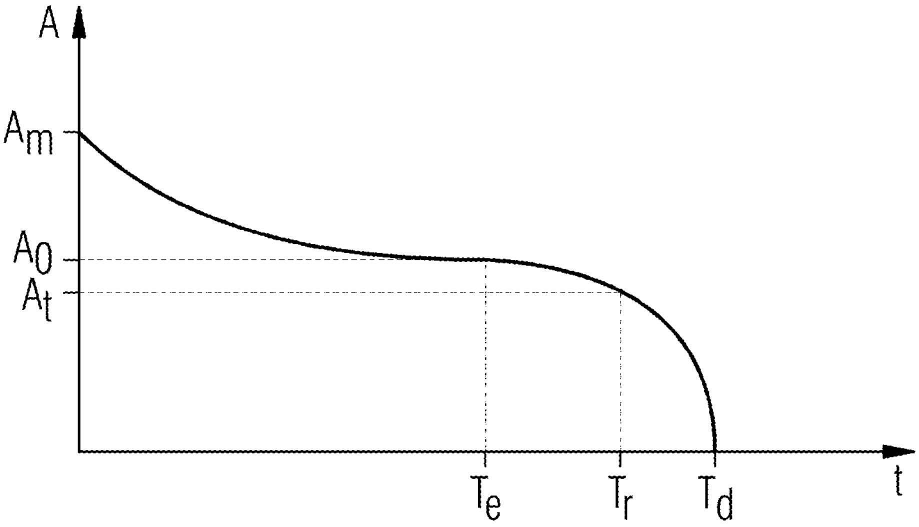
FIG. 10 shows a graphical representation of an award function depending on the time.

In a third step, based on an internal selection, the medical imaging system unit 1 transmits a signal S3 to k (k is a natural number and k<=n) of the remote computing units 2 including information about an acceptance or rejection of their bids. For example, to a number of "a" remote computing units 2 (a is a natural number) a rejection is sent and to a number of b remote computing units 2 (b is a natural number) a proposal acceptance is sent, wherein a+b<=k. In the third step, the winning executor 2 now receives a signal S3 including an offer message that contains the details about the functional definition of the award function A, including already given values of the guaranteed award value $A_0$ and the maximum award value A m as well as the time $T_d$ representing the deadline after which an award value will not be offered. The shape of such function would depend on the mathematical definition. In FIG. 10, an illustrative example of such an award function A is depicted.

In a fourth step, using a signal S4, x remote computing units 2 (x is a natural number and x<=b) send a final commitment message or a proposal withdrawal to the medical imaging system unit 1 and, in case it includes a final commitment message, this message will bind both sides into a contracting obligation.

The executor 2 considers the received offer reflected in key values of an award function A and it bids truthfully its estimation of time $T_e$ needed to execute the given sub-task $T_k$ by replying an ACCEPT message. Should it choose to reject the offer, it will send a REJECT message.

In a fifth step, an answer signal S5 is transmitted to the selected remote computing unit 2 including an information of decline or commit for the compensation of a remote execution of the selected sub-task $T_k$ with a quantitatively defined access to resources. If a requestor 1 intends to proceed with the agreement, it replies with a COMMIT message (arrow with solid line) formally accepting the bid and committing itself for the payment based on agreed award function A. Alternatively, it will reply with a decline message (arrow with dashed line).

As soon as the sub-task $T_k$ is processed, the result will be provided by the executor 2, i.e., the remote computing unit 2, by sending a signal S6, including an INFORM message (arrow with solid line) to the requestor, i.e., the medical imaging system unit 1, and if the task execution is given up, a NO-RESULT message (arrow with dashed line) is transmitted to the requestor 1. In other words, in the sixth step, an answer signal S6 to the answer signal S5 to the selected remote computing unit 2 is received from the selected remote computing unit 2 including an information message comprising the computing result $CR_k$ of the selected sub-task $T_k$ (arrow with solid line) or no result (arrow with dashed line). Time elapsed between transmission of the COMMIT message (signal S5) and reception of the INFORM message (signal S6) is used as the time of result reception $T_r$. This value is crucial to calculate actual award $A_t$ that will be transferred from requestor 1 to executor 2 upon the reception of the task execution result $CR_k$. In the case shown in FIG. 10, time $T_r$ is longer than the estimated time $T_e$, and therefore the award transferred is lower than the agreed value of $A_0$. Should executor 2 perform the sub-task $T_k$ sooner estimated $T_e$, it would receive a value higher than $A_0$, per agreed award function A. As mentioned earlier, the award function shape is agreed upon during negotiation.

In the seventh step, a compensation signal S7, comprising a compensation of the remote execution of the selected sub-task $T_k$ by a quantitatively defined access to resources, is sent to the selected remote computing unit 2. That quantitatively defined access to resources includes the above-mentioned award. If the executor 2, which performed the sub-task $T_k$ is from an internal network system, the award transferred has only an intrinsic value within that network system. In this case, the received award can be used in the future when that executor 2 will undertake a role of a requestor. Such awards can be generated and distributed locally to the executors 2 in form of encrypted award tokens or some sort of cryptocurrency. Accumulation of award values would help the executor to offload more tasks and therefore help in fulfilling the interests of executing its own tasks promptly and optimally in the future. On the other hand, payment to a cloud executor may include an award with actual financial value per contractual obligation with the cloud executor.

Figure 9:
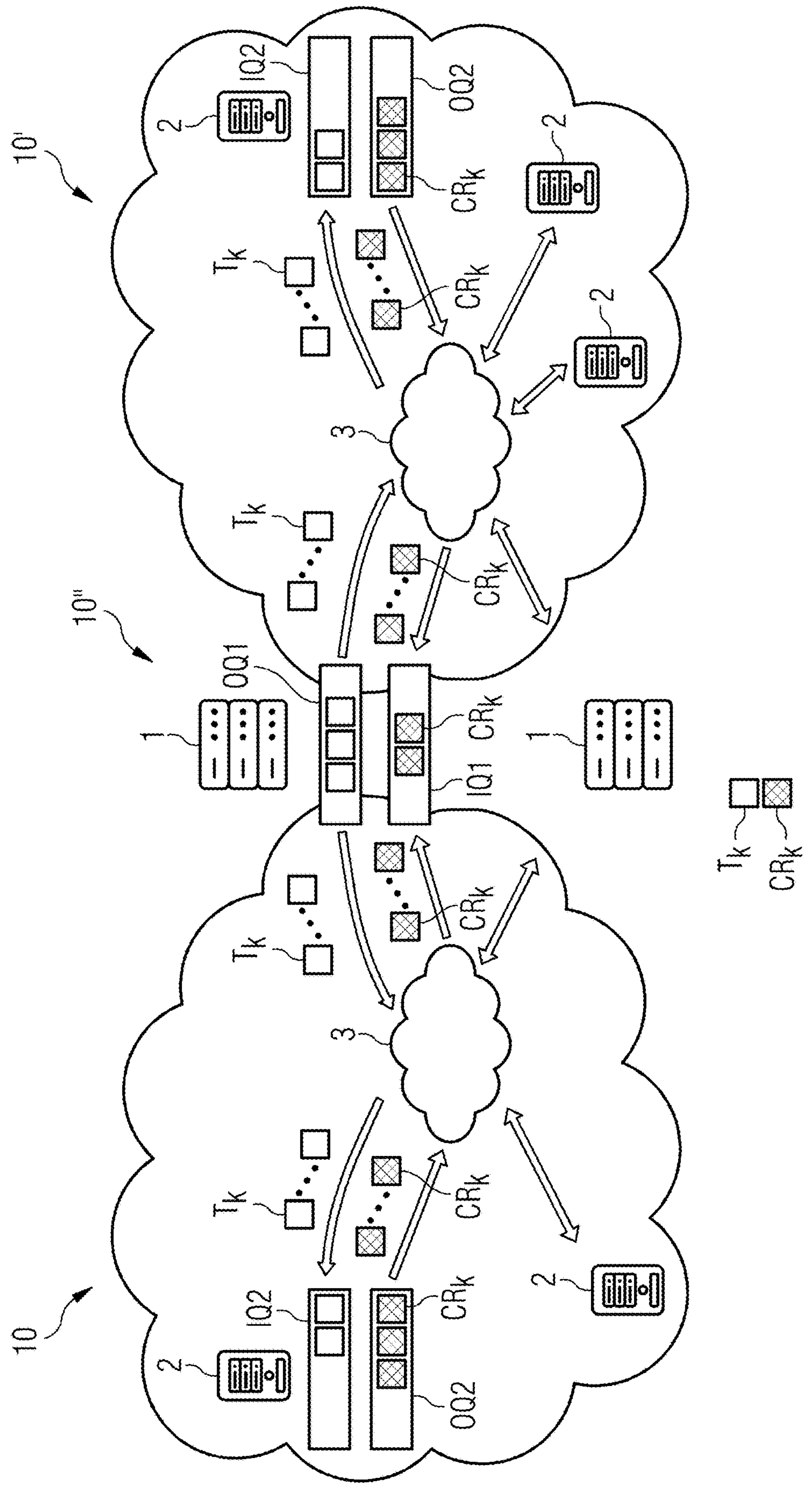
FIG. 9 shows a schematic representation illustrating a medical imaging network according to a second embodiment of the invention.

In FIG. 9, a schematic representation illustrating a medical imaging network 10" according to a second embodiment of the invention is depicted. In contrast to the medical imaging network 10, according to the first embodiment shown in FIG. 7, the medical imaging network 10" includes a local part 10 shown on the left side of FIG. 9 and a global part 10', for example, implemented by a cloud computing system, shown on the right side of FIG. 9. The local part 10 and the global part 10' are substantially illustrated in a mirrored way since the medical imaging system unit 1 is illustrated in the center of FIG. 9.

The local part 10 and the global part 10' comprise a plurality of remote computing units 2 and a distribution unit 3. The distribution unit 3 provides a type of technical distribution node for connecting and assigning requesting medical imaging system units 1 (shown in the center between the local part 10 and the global part 10') and potentially executing remote computing units 2. The medical imaging system units 1 include an output queue OQ1, including sub-tasks $T_k$ to be outsourced to the remote computing units 2 and an input queue IQ1 for receiving results $CR_k$ of executed sub-tasks $T_k$. Correspondingly, each remote computing unit 2 also comprises an input queue IQ2 for receiving sub-tasks $T_k$ to be executed and an output queue OQ2 for outputting results $CR_k$ to the remote medical imaging system units 1 from which the corresponding sub-tasks $T_k$ have been received. The distribution unit 3 receives and distributes these transmitted sub-tasks $T_k$ and results $CR_k$ to the addressed units 1, 2. By integrating the cloud computing system 10' into the medical imaging network 10", high flexibility and scalability of the medical imaging network 10" is achieved.

FIG. 10 shows a graphical representation of an award function A depending on the time t. The shape of the award function A can be arbitrarily chosen by a requestor 1. It typically reflects an urgency and importance of a sub-task $T_k$, e.g., by providing higher $A_0$ and $A_m$ values and/or a steeper functional curve before $T_e$, or a time-sensitivity of the sub-task $T_k$, for example, by providing a hard deadline and no award after $T_e$, where $T_d = T_e$. $A_0$ represents the guaranteed award value, and $A_m$ represents the maximum award value. $T_e$ represents the estimated time for execution of a sub-task $T_k$, $T_r$ is the actual time of result reception or reception time, and $T_d$ represents the deadline after which an award value will not be offered. The value $A_t$ represents the value actually achieved based on the time $T_r$ of result reception. Hence, the "guaranteed award value" $A_0$ is only achieved if the estimated Time $T_e$ is retained.

Figure 11:
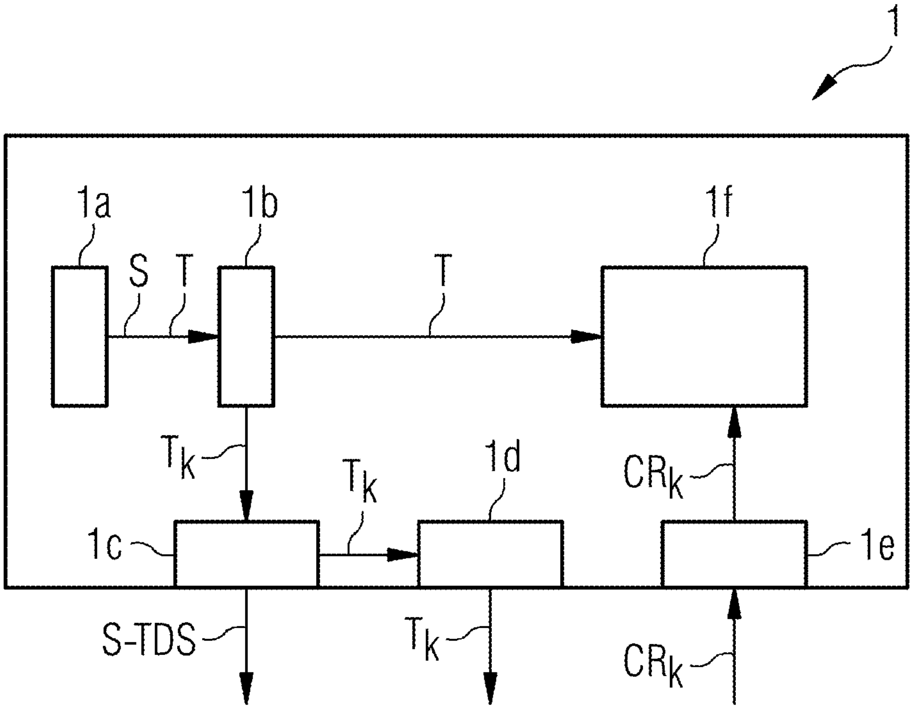
FIG. 11 shows a schematic view of a medical imaging system unit according to an embodiment of the invention.

FIG. 11 shows a schematic view of a medical imaging system 1 unit according to an embodiment of the invention. The medical imaging system unit 1 comprises a division unit 1*a* for dividing a computing task T into a set S of sub-tasks $T_1, \ldots, T_n$.

The medical imaging system unit 1 also comprises a selection unit 1*b* for selecting a sub-task $T_k$ of the sub-tasks $T_1, \ldots, T_n$ for external execution.

Part of the medical imaging system unit 1 is also a communication unit 1*c* for exchanging a sequence S-TDS of task delegation signals TDS with a plurality of remote computing units 2 (not shown in FIG. 11), preferably via a distribution unit 3 (not shown in FIG. 11), for selecting at least one of the remote computing units 2 for execution of the selected sub-task $T_k$.

The medical imaging system unit 1 also comprises an outsourcing unit 1*d* for outsourcing the selected sub-task $T_k$ to the selected remote computing unit 2 (shown in FIG. 12) for remotely generating a computing result $CR_k$ of the selected sub-task $T_k$.

The medical imaging system unit 1 also includes a reception unit 1*e* for receiving the generated partial computing result in $CR_k$ from the selected remote computing unit 2.

Moreover, the medical imaging system unit 1 comprises an execution unit 1*f* for completing the computing task T with the computing result $CR_k$ received from the selected remote computing unit 2.

Figure 12:
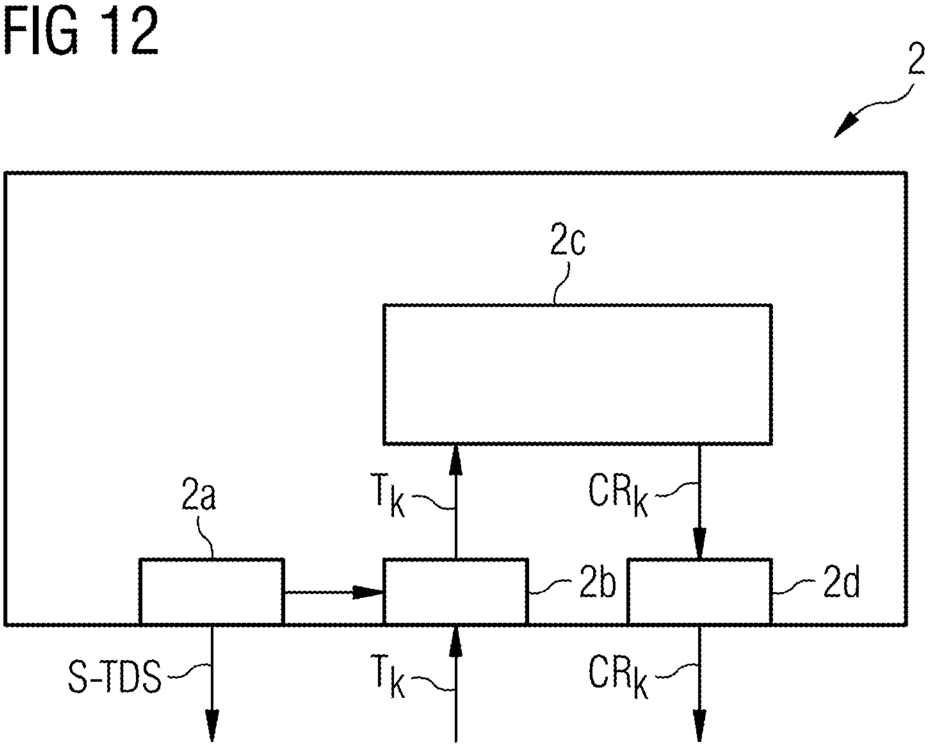
FIG. 12 shows a schematic view of a computing unit for performing a task of a medical imaging system unit according to an embodiment of the invention.

FIG. 12 shows a schematic view of a computing unit 2 for performing a sub-task $T_k$ of a medical imaging system unit 1 according to an embodiment of the invention.

The computing unit 2 comprises a communication unit 2*a* for exchanging a sequence S-TDS of signals with the remote medical imaging system unit 1, preferably over a distribution unit 3 (not shown in FIG. 12), whereby the sequence S-TDS of signals TDS comprises at least a request signal S1 received from the remote medical imaging system unit 1.

Moreover, the computing unit 2 comprises a reception unit 2*b* for receiving the sub-task $T_k$ from the remote medical imaging system unit 1.

The computing unit 2 further comprises an execution unit 2*c* for executing the received sub-task $T_k$ and generating a computing result $CR_k$ of the sub-task $T_k$.

Besides, the computing unit 2 comprises a transmission unit 2*d* for transmitting the computing result in $CR_k$, preferably via the distribution unit 3 (not shown in FIG. 12) to the remote medical imaging system unit 1 (shown in FIG. 11).

The above descriptions are merely preferred embodiments of the present disclosure but not intended to limit the present disclosure, and any modifications, equivalent replacements, improvements, etc., made within the spirit and principle of the present disclosure should be included within the scope of protection of the present disclosure.

Further, the use of the undefined article "a" or "one" does not exclude that the referred features can also be present several times. Likewise, the term "unit" or "device" does not exclude that it consists of several components, which may also be spatially distributed.

The invention claimed is:

1. A method of performing a medical imaging process comprising:

dividing a computing task of a medical imaging system unit into a set of sub-tasks, wherein the computing task is related to a generation of medical image data based on measurement data;

selecting at least one sub-task of the set of sub-tasks for external execution;

exchanging a sequence of task delegation signals with a plurality of remote computing units, via a distribution unit, to select at least one of the remote computing units to execute the selected at least one sub-task using a computational resource allocation process comprising a second-best estimation selection in which one of the plurality of remote computing units is selected for execution of the at least one sub-task based on a service proposal signal of a non-selected remote computing unit, the service proposal signal of the non-selected remote computing unit indicating an estimated execution time for the non-selected remote computing unit to complete the at least one sub-task, and the one of the plurality of remote computing units being selected based on having a shortest estimated execution time from among a plurality of service proposal signals received from the plurality of remote computing units, wherein the one of the plurality of remote computing units is assigned the estimated execution time of the non-selected remote computing unit, the estimated execution time being a next shortest estimated execution time after an estimated execution time of the one of the plurality of remote computing units, and wherein the sequence of task delegation signals comprises at least one request signal sent by the medical imaging system unit;

outsourcing the at least one selected sub-task to the selected remote computing unit to remotely generate a computing result of the at least one selected sub-task;

receiving the generated computing result from the selected remote computing unit; and completing the computing task with the computing result received from the selected remote computing unit.

2. The method according to claim 1, wherein the step of exchanging the sequence of task delegation signals, comprises:

sending a first request signal to the plurality of remote computing units via the distribution unit;

receiving a service proposal signal via the distribution unit from at least one remote computing unit of the plurality of remote computing units;

selecting at least one remote computing unit of the at least one remote computing unit to execute the selected sub-task based on the received service proposal signal;

sending a second request signal for execution of the selected sub-task to the selected remote computing unit; and receiving a commitment signal of the at least one remote computing unit for execution of the selected sub-task.

3. The method according to claim 2, wherein the step of sending the second request signal comprises transmitting an offer signal to the selected remote computing unit with details of a criteria for a quantitatively defined access to resources in exchange for performing a remote execution of the selected sub-task.

4. The method according to claim 3, wherein the criteria includes details about a shape of a functional definition of a time-based resource allocation function.

5. The method according to claim 2, wherein the step of receiving a commitment signal comprises receiving a rejection or acceptance from the selected remote computing unit.

6. The method according to claim 2, wherein the step of exchanging the sequence of signals comprises a sub-step of:

transmitting an answer signal to the selected remote computing unit including information of decline or commit for a quantitatively defined access to resources in exchange for performing a remote execution of the selected sub-task; or receiving an answer signal to the answer signal to the selected remote computing unit from the selected remote computing unit including an information message including the computing result of the selected sub-task or no result; or transmitting a resource allocation signal comprising the quantitatively defined access to resources in exchange for the remote execution of the selected sub-task to the selected remote computing unit.

7. The method according to claim 1, wherein the request signal comprises details about the sub-task to be executed.

8. The method according to claim 2, wherein the service proposal signal comprises an estimated time by which the sub-task is to be executed.

9. The method according to claim 8, wherein the request signal comprises a resource allocation value if the sub-task is executed by the estimated time estimated by the selected remote computing unit, and a maximum resource allocation value if the sub-task is executed earlier.

10. The method according to claim 6, wherein the resource allocation signal is transmitted to the selected remote computing unit, the resource allocation signal comprising the quantitatively defined access to resources in exchange for execution of the selected sub-task.

11. The method according to claim 1, wherein the distribution unit comprises a computer network connecting the medical imaging system unit and the plurality of remote computing units, and wherein at least one of the plurality of remote computing units is spatially separated from the medical imaging system unit.

12. A non-transitory computer program product with a computer program, which is loadable directly into a memory of a medical imaging network, with program sections to perform steps of the method according to claim 1, when the computer program is carried out in the medical imaging network.

13. A non-transitory computer-readable medium, on which program sections that are readable in and executable by a computer are stored in order to carry out steps of the method according to claim 1, when the program sections are executed by the computer.

14. A method of performing a sub-task for a remote medical imaging system unit, comprising:

exchanging a sequence of signals, including task-delegation signals, with the remote medical imaging system unit via a distribution unit using a computational resource allocation process comprising a second-best estimation selection in which a remote computing unit is selected to execute the sub-task based on a service proposal signal of a non-selected remote computing unit, the service proposal signal of the non-selected remote computing unit indicating an estimated execution time for the non-selected remote computing unit to complete the sub-task, and the remote computing unit being selected based on having a shortest estimated execution time from among a plurality of service proposal signals received from a plurality of remote computing units, wherein the remote computing unit is assigned the estimated execution time of the non-selected remote computing unit, the estimated execution time being a next shortest estimated execution time after an estimated execution time of the remote computing unit, and wherein the sequence of signals comprises at least a request signal received from the remote medical imaging system unit;

receiving the sub-task from the remote medical imaging system unit;

executing the received sub-task and generating a computing result of the sub-task; and transmitting the computing result, via the distribution unit, to the remote medical imaging system unit.

15. The method according to claim 14, wherein the step of exchanging a sequence of signals comprises a sub-step of:

receiving a first request signal from the medical imaging system unit via the distribution unit; or sending a service proposal signal, via the distribution unit, to the medical imaging system unit; or receiving a second request signal for execution of the selected sub-task from the medical imaging system unit; or sending a commitment signal for execution of the selected sub-task to the medical imaging system unit.

16. A medical imaging system unit, comprising:

a memory configured to store instructions; and processing circuitry configured to execute the instructions stored in the memory to:

divide a computing task into a set of sub-tasks, wherein the computing task is related to a generation of medical image data based on measurement data;

select a sub-task of the set of sub-tasks for external execution;

exchange a sequence of task delegation signals with a plurality of remote computing units, via a distribution unit, to select at least one of the remote computing units for execution of the selected sub-task using a computational resource allocation process comprising a second-best estimation selection in which a remote computing unit is selected to execute the selected sub-task of the set of sub-tasks based on a service proposal signal of a non-selected remote computing unit, the service proposal signal of the non-selected remote computing unit indicating an estimated execution time for the non-selected remote computing unit to complete the selected sub-task, and the remote computing unit being selected based on having a shortest estimated execution time from among a plurality of service proposal signals received from the plurality of remote computing units, wherein the remote computing unit is assigned the estimated execution time of the non-selected remote computing unit, the estimated execution time being a next shortest estimated execution time after an estimated execution time of the remote computing unit, and wherein the sequence of task delegation signals comprising at least one request signal sent by the medical imaging system unit;

outsource the selected sub-task to the selected remote computing unit to remotely generate a computing result of the selected sub-task;

receive the generated computing result from the selected remote computing unit; and complete the computing task with the computing result received from the selected remote computing unit.

17. A computing unit for performing a sub-task for a remote medical imaging system unit, comprising:

a memory configured to store instructions; and processing circuitry configured to execute the instructions stored in the memory to:

exchange a sequence of signals with the remote medical imaging system unit over a distribution unit using a computational resource allocation process comprising a second-best estimation selection in which a remote computing unit is selected to execute the sub-task based on a service proposal signal of a non-selected remote computing unit, the service proposal signal of the non-selected remote computing unit indicating an estimated execution time for the non-selected remote computing unit to complete the sub-task, and the remote computing unit being selected based on having a shortest estimated execution time from among a plurality of service proposal signals received from a plurality of remote computing units, wherein the remote computing unit is assigned the estimated execution time of the non-selected remote computing unit, the estimated execution time being a next shortest estimated execution time after an estimated execution time of the remote computing unit, and wherein the sequence of signals comprising at least a request signal received from the remote medical imaging system unit;

receive the sub-task from the remote medical imaging system unit;

execute the received sub-task and generate a computing result of the sub-task; and transmit the computing result, via the distribution unit, to the remote medical imaging system unit.

* * * * *